United States Patent [19]

Workman

[11] 4,032,789

[45] June 28, 1977

[54] MEANS FOR CONTROLLING OPERATION OF POWER SOURCES ASSOCIATED WITH AN AXIAL TOMOGRAPHIC SYSTEM

[75] Inventor: Samuel Thomas Workman, Los Gatos, Calif.

[73] Assignee: Syntex (U.S.A.) Inc., Palo Alto, Calif.

[22] Filed: Oct. 28, 1975

[21] Appl. No.: 625,806

[52] U.S. Cl. .......................... 250/445 T; 250/402; 250/414

[51] Int. Cl.² .......................................... G03B 41/16

[58] Field of Search .............. 250/445 T, 401, 402, 250/408, 409, 416, 413, 414

[56] References Cited

UNITED STATES PATENTS

| | | | |
|---|---|---|---|
| 3,770,963 | 11/1973 | Vandervelden | 250/409 |
| 3,866,047 | 2/1975 | Hounsfield | 250/445 T |

Primary Examiner—Craig E. Church
Attorney, Agent, or Firm—Joseph I. Hirsch; William B. Walker

[57] ABSTRACT

An axial tomographic system having scanner means normally in an "off" condition where all power sources associated therewith are electrically isolated from the units driven thereby, means for activating the scanner means to establish an "on" condition, control means including means to measure one or more system parameters when the scanner means is in an "on" condition and to determine if the measured parameters are within predetermined limits therefor, and means for maintaining the "on" condition only if the control means is properly operational and all measured system parameters are within the predetermined limits therefor.

22 Claims, 1 Drawing Figure

MEANS FOR CONTROLLING OPERATION OF POWER SOURCES ASSOCIATED WITH AN AXIAL TOMOGRAPHIC SYSTEM

FIELD OF THE INVENTION

This invention relates to radiation diagnostics. More particularly it relates to an axial tomographic system having means for automatically maintaining operation of the power sources associated therewith only if a central control means remains properly operational and all measured system parameters are within the predetermined limits therefor.

BACKGROUND OF THE INVENTION

In U.S. Pat. No. 3,778,614 there is described a method and apparatus for examining an object by means of X- or $\gamma$-radiation. A commercial embodiment thereof has a source of X-rays adapted to transmit a beam of radiation through a planar slice of the object to be examined, detector means to detect the transmitted beam after it has passed through the object and means to sequentially translate and rotate the source and detector means about the object during radiographic examination. If there is a malfunction with this commercial embodiment and/or a measured parameter is determined to be outside the predetermined limits therefor, the associated computer automatically turns off the radiation source and registers this operation on a main control console. However, it is not clear that operation of the radiation source is terminated in the event of a computer malfunction, since the computer must order shut down of the source. In such a case, the object being examined, such as a patient, would unnecessarily be subjected to further radiation. Accordingly, it would be desirable to have an axial tomographic system which is not subject to the aforesaid deficiency.

OBJECTS OF THE INVENTION

It is, therefore, the primary object of this invention to provide a novel axial tomographic system.

It is a further object of this invention to provide a novel axial tomographic system having means for controlling the operation of various power sources associated therewith.

It is a further object of this invention to provide a novel axial tomographic system which is normally in the "off" condition, the system having means associated therewith for maintaining operation thereof only if central control means is operational and all measured system parameters are within the predetermined limits therefor.

Yet a still further object of the present invention is to provide a novel axial tomographic system wherein central control means sends a series of periodic signals to the power sources associated with the system for maintaining operation thereof, and, if the signals are not received by the various power sources, they are automatically electrically isolated from the units driven thereby.

These and still further objects, features and advantages of the present invention will become apparent upon consideration of the following detailed disclosure.

BRIEF SUMMARY OF THE INVENTION

These and still further objects, features and advantages of the present invention are achieved, in accordance therewith, by providing an axial tomographic system having scanning means which is normally maintained in the "off" condition, the system having means associated therewith for maintaining the scanning means in an established "on" condition only if a central control means is properly operational and all measured system parameters are within the predetermined limits therefor. Various means associated with the operation-maintaining means permit a signal from the central control means to return thereto only if a parameter measured by each of such various means is within the predetermined limits therefor. Other means associated with the operation-maintaining means measure various system parameters and send the data resulting from such measurements to the central control means for processing to determine if the parameters are within the predetermined limits therefor. The central control means sends a series of periodic signals to the various power sources associated with the scanning means to maintain operation thereof only if the central control means is properly operational (and thus can send the operation-maintaining signals) and all measured system parameters are within the predetermined limits therefor. Thus, if the central control means is not operational and any measured system parameter is outside the predetermined limits therefor, the power sources are automatically electrically isolated from the units driven thereby due to the failure of the power sources to receive an operation-maintaining signal from the central control means.

It should be clearly understood that the axial tomographic system of this invention is normally maintained in an "off" condition, and after manual activation of the system to establish an "on" condition, the system is maintained in the "on" condition only if the central control means remains properly operational and all system parameters are within the predetermined limits therefor. This is achieved by causing the central control means to send a series of frequent, periodic operation-maintaining signals to each of the power sources associated therewith. If there is a malfunction with the central control means or any measured system parameter is outside of the predetermined limits therefor, there is an interruption in the transmission of the operation-maintaining signals and the system returns to its normal "off" condition. In this manner, the object being examined is not exposed to unnecessary radiation should there be a system malfunction.

In one particular aspect of this invention, the axial tomographic system includes scanner means having frame means having an opening therein for receiving an object to be examined, a source of penetrating radiation and detector means mounted on the frame means for directing one or more beams of penetrating radiation from the source to the detector means, a power source for the source of penetrating radiation, means to rotate the frame means including the source and the detector means mounted thereon about the opening, and a power source for the rotation means; and means to control the operation of the scanner means, the control means including central control means and (a) reference detector means to measure the intensity of radiation emanating from the source, (b) angular encoder means to determine the position of the frame means after each rotation thereof, (c) means to measure the response of the detector means to radiation emanating from the source, and means associated with each of the means (a)–(c) for sending the data measured thereby to the central control means to determine if the parameters measured thereby are within the predetermined limits therefor, the central control means being adapted to send a series of periodic signals to the scanner power sources to maintain operation thereof only if the central control means is properly operational and all measured system parameters are within the predetermined limits therefor, whereby if the central control means is not operational or any measured system parameter is outside the predetermined limits therefor, the scanner power sources are automatically isolated from the units driven thereby due to failure of each power source to receive an operation-maintaining signal from the central control means. This aspect of the invention is generally applicable to all axial tomographic systems where it is desired to monitor the aforesaid parameters.

In a further aspect of the invention, the scanner means further includes means to measure the current and voltage applied to the source power source and means to monitor the temperature of the source, and the control means further includes (d) means to send a signal to the current and voltage measuring means, and (e) means to send a signal to the temperature monitoring means, and means associated with each of means (d) and (e) to permit the respective signals from the central control means to return thereto if the parameter measured thereby is within the predetermined limits therefor. If any parameter is outside the prescribed limits, the signal from the central control means does not return thereto, the sending of further operation-maintaining signals to the scanner power sources is interrupted, whereby the system returns to the normal "off" condition where units driven by the various power sources are electrically isolated therefrom.

In yet a further aspect of this invention, which is applicable to either or both of the aspects described in the two preceding paragraphs, the control means further includes (f) linear encoder means to determine the positioning and translational velocity of the source and means associated therewith to determine if such parameters are within the predetermined limits therefor. This aspect of the invention is particularly applicable to axial tomographic systems where the source is both rotated about, and translated across the lateral width of, the planar slice of the object being examined (e.g., the systems described by U.S. Pat. No. 3,778,614 and in FIG. 1 hereof).

If desired, means can be provided to determine that any doors to the examination room are closed during examination, that the drift of the scanner clock relative to the central control means clock is within prescribed limits, etc. As with the other system parameters, if any of these further parameters are determined to be outside the prescribed limits therefor, the necessary operation-maintaining signals are not sent and the system returns to the normal "off" condition.

In essence, the system described herein provides that the central control means send a signal or pulse, at frequent periodic intervals, to the scanner power sources to maintain the operation thereof. If, for any reason, this signal is not sent by the central control means, the power sources, and thus the scanner means, is returned to its normal "off" condition where the units driven by the power sources are electrically isolated therefrom. No operator intervention is required as the shut-down is automatic, and, in addition, this system is automatically responsive to malfunction of the central control means per se since, with such a malfunction, the necessary operation-maintaining signal or pulse can not be sent and thus operation of the scanner means is not maintained.

The series of control measurements and determinations carried out by the system described herein are preferably conducted in a series of stages, which are then repeated throughout operation of the system until such time as system operation is automatically terminated at the end of the examination, or there is a system malfunction where system operation is not further maintained. This will be described in further detail below.

BRIEF DESCRIPTION OF THE DRAWING

The features and advantages of the present invention will become more apparent from the following detailed description, taken together with the accompanying drawing wherein:

Referring to FIG. 1, there is shown the scanner portion 10 of an axial tomographic system 12 including an X-ray source 14 which directs a fan-shaped beam 16 of X-rays through a planar slice of an object 18 (for example the head or body portion of a patient) which is to be examined. As shown, the object may be surrounded by a support 20 which is generally filled with water, the support, in turn, being surrounded by a plastic block (not shown). The plastic block has a cylindrical opening therein which surrounds the outside of the support 20 and rotates around the support which remains stationary along with the object during the radiographic procedure. A collimator 22 between source 14 and object 18 collimates the beam of X-rays into a fan-shaped array of a plurality of smaller beams, for example, 12 smaller beams each having a depth (direction into the paper) of about 1 centimeter and a thickness in the plane of the fan of about 1.2 millimeters. A reference detector 23 associated with collimator 22 measures the intensity $I_r$ of the radiation emanating from source 14 and sends a signal corresponding to this measurement to central control means 36. A collimator 24 between object 18 and detector means 26 reduces detection of Compton scattered radiation emanating from the object undergoing analysis. Detector means 26 can have, for example, an array of photon detectors disposed at the output end of collimator 24 to detect individual beams of radiation passing through object 18 and collimator 24 to the respective detectors. The output from the various detectors is fed, by known means in a known manner, to a data storage and processing means (not shown) which may also be central control means 36.

Figure 1:
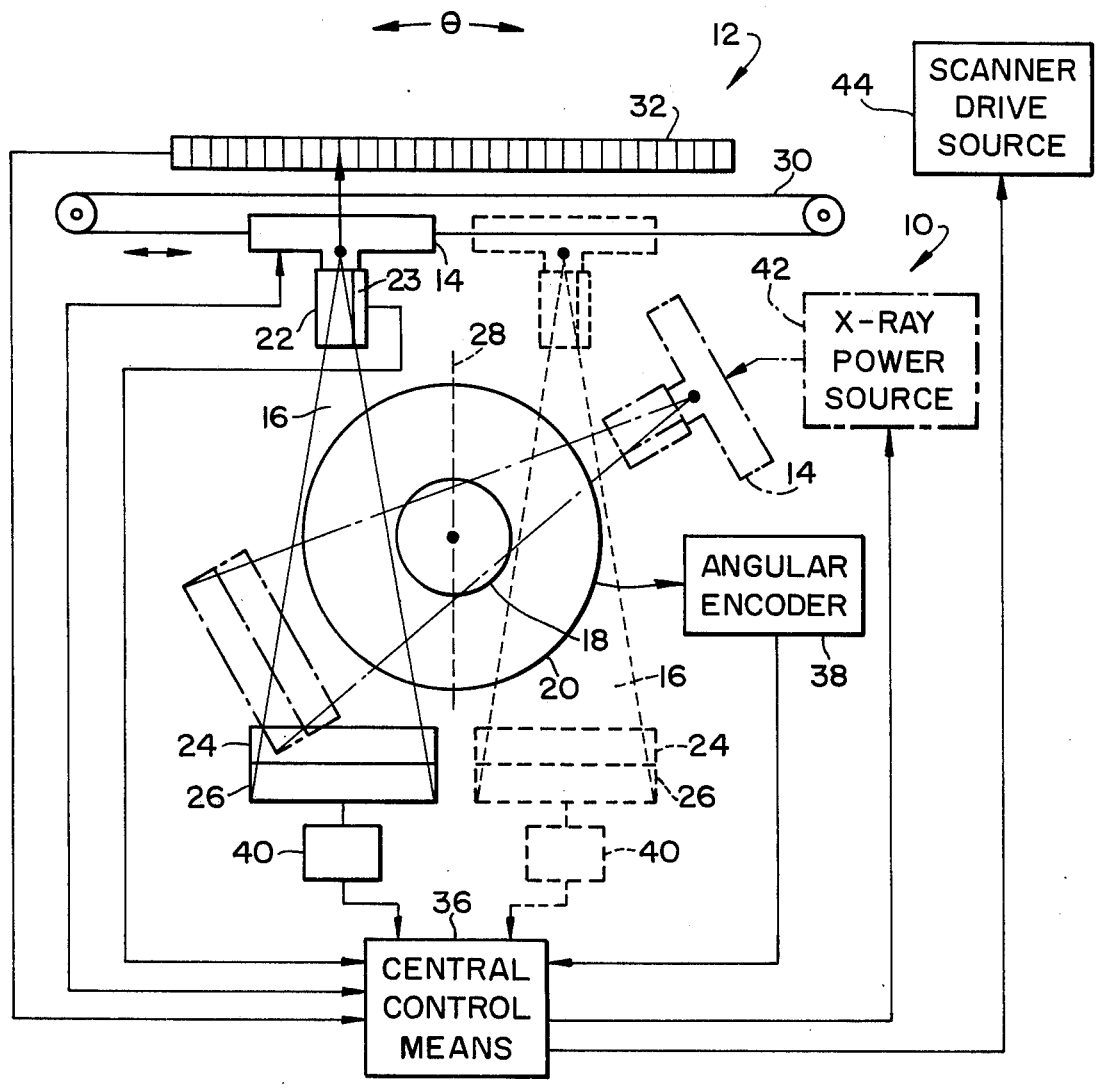
FIG. 1 is a schematic representation of an axial tomographic system exemplifying the fail-safe control means of the present invention.

In the embodiment shown in FIG. 1. scanner 10 both rotates and translates about object 18 to be analyzed. Scanner 10 rotates about an axis of revolution 28 which preferably passes through the central region of the planar slice of the object being examined, the angular rotation of scanner 10 being indicated by the angle $\theta$ on the drawing. Additionally, the fan-shaped beam of rotation is scanned laterally across object 18 for each angular orientation of scanner 10. In an exemplary system, detector means 26 has 12 individual detectors at 1° angular spacings, and scanner 10 is rotated in successive 12° increments about object 18. Between successive rotations, source 14 and detector 26 on opposite sides of object 18 are translated across the lateral dimension of the object being analyzed by means of belt drive 30, and the precise lateral positioning of source 14 is detected by optically read lateral position encoder 32, the output of which is fed to central control means 36. One lateral extreme of the lateral traverse is shown in solid outline while the other lateral extreme is shown in dashed (---) outline. The time for source 14 to traverse between these two positions is measured by a clock associated with central control means 36. By correlating the distance with the time to travel that distance, the translational velocity of source 14 can be determined by central control means 36. The angular orientation of scanner 10 is determined by angular position encoder means 38, and the intensity of radiation reaching each of the detectors is measured by detector monitoring means 40 and a signal corresponding to each of these measurements is sent to central control means 36. The above signals received by central control means 36 are compared with data stored therein to determine if the various measured parameters are within the prescribed limits therefor.

In addition to the above system checks, central control means 36 sends a signal to X-ray generator (not shown). If the temperature of the coolant associated therewith is within the prescribed limits, the signal returns to central control means 36. In a similar manner, central control means 36 sends a signal to X-ray source 14. If the current and voltage applied to source 14 are within the prescribed limits, the signal returns to the central control means.

When activated to the "on" condition from its normal "off" condition, as by a command from an operator immediately prior to the beginning of an examination, central control means 36 sends operation-maintaining signals to source power source 42 [shown in dotted (——)outline for ease of graphical representation] and scanner drive source 44 (although actual operation of the scanner may not yet have begun). Central control means 36 continues to send these signals if it is itself properly operational and all other measured system parameters are within the prescribed limits therefor. If, however, central control means 36 is not operational (as by a malfunction or power shortage associated therewith) or any of the system parameters is outside of the prescribed limits, power sources 42 and 44 are automatically isolated from the units they drive due to the failure of central control means 36 to send further operation-maintaining signals. In this manner, the failure of any component of the system which is being monitored or of the central control means itself automatically returns the scanner to its normal "off" condition, thereby minimizing exposure of the object to unnecessary radiation.

In operation, when the operator activates the system, for example to commence an examination, the central control means first determines that certain items are in proper order. These items may include, for example, that sufficient cooling oil is being supplied to the X-ray tube for cooling thereof, that the clock in the central control means is operational, that power is on to all subsystems, and, optionally, that the door to the examination room is closed so that X-rays do not pass into undesired areas. If these first series of items are determined to be operating properly, the central control means allows all power sources associated with the scanner to be energized for a short interval of time. During this short interval, the control means conducts a second series of determinations. More particularly, the control means determines that the radiation as detected by the reference detector is within the prescribed limits, that proper voltage and current are being applied to the X-ray source and that the scanner clock is operational. At this time, a series of short interval (e.g., 1 second or less) pulses are sent to the various power sources, e.g., the power source for the scanner drive, and the power source for the X-ray tube. An operational failure of the central control means or other malfunction of the system interrupts the sending of further pulses whereby the system returns to its normal "off" condition where all power sources associated with the scanner are electrically isolated from the units they drive. If, however, the central control means is properly operational and all measured system parameters are within the prescribed limits therefor, the scanner starts a lateral traverse of the object wherein the X-ray source is moved laterally across the object. At this point, a third set of determinations are executed by the central control means. More particularly, this third set of determinations includes checking that all individual detectors are within proper operating ranges, that the lateral velocity of the source is within the prescribed limits therefor, and that upon termination of a given lateral scan the scanner has actually rotated to the next desired position. If these steps have been properly conducted, the central control means continues to send the sequence of short interval pulses adapted to maintain the system in the "on" condition. These three series of checks are continuously conducted until such time as the examination is completed (and the system naturally returns to its "off" condition) or until there is a system malfunction which precludes the sending of the operation-maintaining signals whereby the system returns to its normal "off" condition where all power sources associated with the scanner are electrically isolated from the units they drive. In this manner, it is assured that the object being examined will not be subjected to unnecessary radiation at a time when a system malfunction has occurred.

The control techniques and means described herein are applicable for use in conjunction with axial tomographic systems of diverse configurations. For example, in one configuration the scanner has a source X- or γ-radiation adapted to transmit a beam of radiation through a planar slice of the object to be examined, detector means to detect the transmitted beam after it has passed through the object, and means to sequentially translate and rotate the source and detector means about the object during the radiographic examination. Such a scanner is shown, for example, by U.S. Pat. No. 3,778,614. In a different configuration, as shown by copending application Ser. No. 528,026, filed Nov. 29, 1974, in the name of Douglas Boyd et al, a fan-shaped beam of penetrating radiation is directed through the slice of the object to be analyzed to radiation-sensitive detector means having a plurality of individual detectors for deriving a set of data corresponding to the transmission or absorption of the penetrating radiation by the object along a plurality of divergent lines extending from the source to the detector. A number of sets of such data are obtained for different angles of rotation of the fan-shaped beam relative to the center of the slice being analyzed, without lateral translation of the source and detection means between successive rotation of the fan-shaped beam. Fan-beam irradiation can also be used, however, in conjunction with scanners which require lateral translation of the source and detector, as described, for example, in FIG. 1 hereof. The present invention is applicable for use in conjunction with any of the aforesaid configurations, other computerized axial tomographic configurations which may differ from the above configurations, or other X-ray or γ-ray diagnostic apparatus and configurations which desirably should include control means for limiting the exposure of the object being examined to unnecessary radiation. It should be understood, however, that certain of the monitoring units described above may be unnecessary with regard to a particular configuration; for example, in a pure rotary, fan-beam system as described by Boyd et al, a transverse linear encoder and associated positioning and velocity determining means would not be needed. In addition, however, other interlocks, such as for monitoring the temperature of the coolant for an X-ray source, that all doors to the examination (e.g., scanner) room are closed, or remain closed, during X-ray exposure, etc., may be utilized if desired or required by governmental regulation.

Specific electronic circuitry and elements for the implementation of the present invention are considered to be well-known and/or within the skill of those skilled in this art in view of this disclosure and, accordingly, form no part of this invention and will not be described in specific detail.

U.S. Pat. No. 3,778,614 and copending applications Ser. No. 528,026, filed Nov. 29, 1974 and Ser. No. 625,805, filed Oct. 28, 1975, are incorporated herein by reference to the extent necessary to complete, or render fully understandable, the disclosure hereof.

While this invention has been described with reference to specific embodiments thereof, it should be understood by those skilled in this art that various changes may be made and equivalents may be substituted without departing from the true spirit and scope of the invention. All such modifications are intended to be within the scope of the claims appended hereto.

What is claimed is:

1. An axial tomographic system including scanner means for collecting a plurality of sets of data corresponding to the transmission or absorption of one or more beams of penetrating radiation through a planar slice of an object to be examined, said scanner means including one or more power sources associated therewith, said scanner means adapted to automatically return to the "off" condition during scanning operation if not maintained in the "on" condition; means for activating said scanner means to establish an "on" condition to thereby enable scanning operation to occur; and control means including means to measure one or more system parameters when said scanner means is in the "on" condition and to determine if the measured parameters are within predetermined limits therefor, and means for maintaining said "on" condition only if said control means is properly operational and all measured system parameters are within the predetermined limits therefor, said means for maintaining the "on" condition including means to send a series of periodic operation-maintaining signals to each of said power sources, said operation-maintaining signals being sent only if said control means is properly operational and all measured system parameters are within the predetermined limits therefor, whereby, if said control means is not operational or any measured system parameter is outside the predetermined limits therefor, said power sources are automatically electrically isolated from the units driven thereby due to failure of said power sources to receive an operation-maintaining signal from said signal-sending means.

2. The system of claim 1 wherein when said scanner means is in an "off" condition all power sources associated therewith are electrically isolated from the units driven thereby.

3. The system of claim 1 wherein said scanner means includes frame means having an opening therein for receiving an object to be examined, a source of penetrating radiation and detector means mounted on said frame means for directing one or more beams of penetrating radiation from said source to said detector means, and means to rotate said frame means including said source and said detector means mounted thereon about the opening.

4. The system of claim 3 wherein said measuring means includes (a) reference detector means to measure the intensity of radiation emanating from said source of penetrating radiation, (b) angular encoder means to determine the angular position of said frame means, (c) means to measure the response of said detector means to radiation emanating from said source of penetrating radiation, and means associated with each of said means (a)-(c) for sending the data measured thereby to said control means to determine if the parameters measured thereby are within the predetermined limits therefor.

5. The system of claim 4 wherein said measuring means further includes (d) means to measure the current and voltage applied to said penetrating radiation power source and (e) means to monitor the temperature of said source of penetrating radiation, said control means further including means to send a signal to said current and voltage measuring means (d) and means to send a signal to said temperature monitoring means (e), and means associated with each of said means (d) and (e) to permit the respective signals from said control means to return thereto if the parameter measured thereby is within the predetermined limits therefor.

6. The system of claim 3 wherein said source of penetrating radiation directs a divergent beam of penetrating radiation from said source to said detector means.

7. The system of claim 3 wherein said source of penetrating radiation directs a divergent, planar, fan-shaped beam of penetrating radiation from said source to said detector means.

8. The system of claim 3 wherein said source of penetrating radiation directs one or more substantially pencil-shaped beams of radiation from said source to said detector means.

9. The system of claim 3 wherein said means for rotating said frame means effects relative angular displacement between the beam of penetrating radiation and the object in a manner which is substantially free of lateral translation therebetween.

10. The system of claim 3 wherein said scanner means further includes means to translate said source laterally across the opening between successive rotations of said frame means by said rotation means.

11. The system of claim 10 wherein said measuring means includes (a) reference detector means to measure the intensity of radiation emanating from said source of penetrating radiation, (b) angular encoder means to determine the angular position of said frame means, (c) means to measure the response of said detector means to radiation emanating from said source of penetrating radiation, (f) linear encoder means to determine the positioning and translational velocity of said source of penetrating radiation, and means associated with each of said means (a)-(c) and (f) to determine if the parameters measured thereby are within the predetermined limits therefor.

12. The system of claim 10 wherein said measuring means includes linear encoder means to determine the positioning and translational velocity of said source of penetrating radiation, and means associated therewith to determine if such parameters are within the predetermined limits therefor.

13. The system of claim 1 wherein said control means includes means to measure a first set of system parameters to determine if the first set of measured parameters are within the predetermined limits therefor, means to energize all power sources associated with said scanner means for a short interval of time if the first set of measured parameters are within the predetermined limits therefor, and means, operative within said short interval of time, to measure a second set of system parameters to determine if the second set of measured parameters are within the predetermined limits therefor, whereby, if the first and second sets of system parameters are within the predetermined limits therefor, operation-maintaining signals are sent by said signal-sending means to maintain said system in the "on" condition.

14. The system of claim 13 further including means to measure a third set of system parameters to determine if the third set of measured parameters are within the predetermined limits therefor as said scanning means moves about the planar slice of the object being examined, whereby, if all measured system parameters are determined to be within the predetermined limits therefor, said operation-maintaining signals are sent by said signal-sending means to maintain said scanner means in the "on" condition.

15. The system of claim 14 wherein said three sets of determinations are repeated continuously throughout the examination of the planar slice of the object being examined until such time as the examination is completed or a system malfunction causes the system to return to its normal "off" condition by automatic interruption of the sending of the operation-maintaining signals.

16. An axial tomographic system including scanner means having frame means having an opening therein for receiving an object to be examined, a source of penetrating radiation and detector means mounted on said frame means for directing one or more beams of penetrating radiation from said source to said detector means, a power source for said source of penetrating radiation, means to rotate said frame means including said source of penetrating radiation and said detector means mounted thereon about the opening, and a power source for said rotation means, said scanner means adapted to automatically return to the "off" condition during scanning operation if not maintained in the "on" condition; means to activate the scanner means to establish an "on" condition to thereby enable scanning operation to occur; and control means including means to measure a plurality of system parameters when said scanner means is in the "on" condition including (a) reference detector means to measure the intensity of radiation emanating from said source of penetrating radiation, (b) angular encoder means to determine the angular position of said frame means, (c) means to measure the response of said detector means to radiation emanating from said source of penetrating radiation, and means associated with each of said means (a)-(c) for sending the data measured thereby to said control means to determine if the parameters measured thereby are within the predetermined limits therefor, said control means further including means to send a series of frequent, periodic operation-maintaining signals to said power sources to maintain said scanner means in the "on" condition, said operation-maintaining signals being sent only if said control means is properly operational and all measured system parameters are within the determined limits therefor, whereby if said control means is not operational or any measured system parameter is outside the predetermined limits therefor, said power sources are automatically electrically isolated from the units driven thereby due to failure of said power sources to receive an operation-maintaining signal from said signal-sending means.

17. The system of claim 16 wherein said source of penetrating radiation directs a divergent beam of penetrating radiation from said source of penetrating radiation to said detector means.

18. The system of claim 16 wherein said source of penetrating radiation directs a divergent, planar, fan-shaped beam of penetrating radiation from said source of penetrating radiation to said detector means.

19. The system of claim 16 wherein said measuring means further includes (d) means to measure the current and voltage applied to said penetrating radiation power source and (e) means to monitor the temperature of said source of penetrating radiation, said control means further including means to send a signal to said current and voltage measuring means (d) and means to send a signal to said temperature monitoring means (e), and means associated with each of said means (d) and (e) to permit the respective signals from said control means to return thereto if the parameter measured thereby is within the predetermined limits therefor.

20. The system of claim 16 wherein said scanner means further include means to translate said source of penetrating radiation and said detector means laterally across the opening between successive rotations of said frame means; said control means further including (f) linear encoder means to determine the positioning and translational velocity of said source of penetrating radiation, and means associated therewith to determine if such parameters are within the predetermined limits therefor.

21. The system of claim 20 wherein said source of penetrating radiation directs a divergent beam of penetrating radiation from said source of penetrating radiation to said detector means.

22. The system of claim 20 wherein said source of penetrating radiation directs a divergent, planar, fan-shaped beam of penetrating radiation from said source of penetrating radiation to said detector means.

* * * * *